United States Patent

Jeon

[11] Patent Number: 5,877,841
[45] Date of Patent: Mar. 2, 1999

[54] APPLICATION AND METHOD FOR SELF EYE EXAMINATION USING A VIDEO APPLIANCE

[75] Inventor: Sang Chel Jeon, Kumi, Rep. of Korea

[73] Assignee: LG Electronics, Inc., Seoul, Rep. of Korea

[21] Appl. No.: 757,126

[22] Filed: Dec. 3, 1996

[30] Foreign Application Priority Data

Dec. 5, 1995 [KR] Rep. of Korea .................. 1995-46721

[51] Int. Cl.$^6$ ..................................... A61B 3/02
[52] U.S. Cl. ........................... 351/237; 351/239; 351/246
[58] Field of Search .................................. 351/200, 222, 351/237, 239, 243, 246

[56] References Cited

U.S. PATENT DOCUMENTS

4,611,893  9/1986  Schrier .................................... 351/239
4,998,820  3/1991  Salibello et al. ......................... 351/239

*Primary Examiner*—Huy Mai
*Attorney, Agent, or Firm*—Fish & Richardson P.C.

[57] ABSTRACT

Apparatus and method for eye examination by a video appliance which enables a person to conduct an eye examination, whenever required, especially by means of a remote controller. According to the apparatus, if a user sets an eye examination mode by an eye examination mode key in the remote controller, eye examination data including Landolt Circles which has been stored in a control section, is displayed on a screen of a color picture tube (CPT) through an OSD control section. The control section then controls the OSD control section to adjust the set eye examination data to conform to an eye examination distance and an eyesight level voluntarily determined by the user and to display the adjusted data on the CPT screen of the video appliance.

17 Claims, 7 Drawing Sheets

| EYE-SIGHT | WIDTH X LENGTH | DATA | WIDTH X LENGTH | DATA | WIDTH X LENGTH | DATA |
|---|---|---|---|---|---|---|
| 0.0 ~ 0.9 | ← THE SIZE BECOMES LARGER | | | | | |
| 1.0 | 7.5mm X 7.5mm | (RANDOLT CIRCLE) 7.5mm, 1.5mm, 1.5mm, 1.5mm | LESS THAN 7.5mm X LESS THAN 7.5mm | | MORE THAN 7.5mm X MORE THAN 7.5mm | |
| 1.1 ~ 2.0 | THE SIZE BECOMES SMALLER → | | | | | |
| | DISTANCE = 5m | | DISTANCE < 5m | | DISTANCE > 5m | |

*NOTE: THE DATA OF WIDTH X LENGTH IS DETERMINED BY EXPERIMENTAL METHODS.

| | |
|---|---|
| FIG. 8A<br>EYE EXAM. MODE<br>START  END<br>START : VOL +, -<br>END : CH +, - | FIG. 8E<br>SELECTION OF EYE<br>EXAM. METHOD<br>LIST : 1<br>DIRECT : 2 |
| FIG. 8B<br>DISTANCE ADJ. MODE<br>AUTOMATIC MODE: VOL +, -<br>MANUAL MODE : CH +, - | FIG. 8F<br>CA3 |
| FIG. 8C<br>PLS ENTER YOUR EYESIGHT<br>INPUT : 0 ~ 9<br>COMPLETION : CH +, - | FIG. 8G<br>3 |
| FIG. 8D<br>PLS ENTER YOUR EYESIGHT<br>DISTANCE : 5m<br>INPUT : 0 ~ 9<br>COMPLETION : CH +, - | FIG. 8H<br>YOUR EYESIGHT IS :<br>☐.☐<br>RE-EXAMINATION : VOL +, -<br>END : CH +, - |

APPLICATION AND METHOD FOR SELF EYE EXAMINATION USING A VIDEO APPLIANCE

BACKGROUND OF THE INVENTION

1. Field of the Invention

The present invention relates to an apparatus and method for eye examination by a video appliance, such as a television receiver or monitor, particularly to an apparatus for eye examination by a video appliance which can display an eye examination table corresponding to the distance between the screen of the video appliance and the user as well as the level of the user's eyesight on the screen of the video appliance when an eye examination mode is set.

2. Description of the Prior Art

Figure 1:
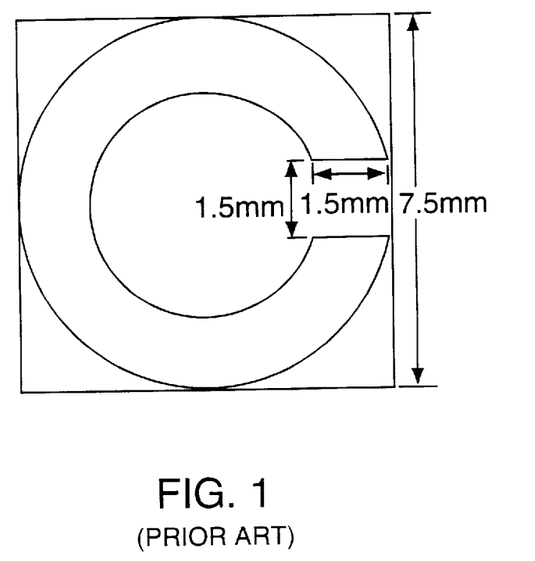
FIG. 1 is a top plan view illustrating a Landolt Circle for eye examination.

FIG. 1 shows the universal eye examination method which uses a standard eyesight indicator featuring an open circle (a Landolt Circle) with a diameter of 7.5 mm and width of 1.5 mm. According to that method, eyesight 1.0 is defined as when a person under eye examination cannot discern the opening of Landolt Circles sized smaller than the standard eyesight indicator from a distance of 5 meters. Eyesight 0.5 is defined when the person cannot discern the opening of Landolt Circles sized up to twice as large as the standard eyesight indicator.

Conventionally, a person desiring to examine his/her own eyesight would resort to either ophthalmic clinics or other places where eye examination tables are used without a TV or monitor as in the aforementioned eye examination apparatus of the present invention. It would accordingly be very convenient if the eye examination could be conducted using an easily-accessible television receiver (TV) or monitor.

SUMMARY OF THE INVENTION

The object of the present invention is to eliminate the aforementioned inconvenience of having to go to a conventional eye examination location, and to provide an apparatus and method for eye examination by a video appliance, particularly by means of a remote controller employing keys for eye examination which can adjust an eye examination table preset in the video appliance according to the distance between the screen of the video instrument and the user as well as of the user's eyesight so that the eye examination table may be automatically displayed on the screen.

In one aspect of the present invention, there is provided an apparatus for eye examination for a video appliance, comprising:

key input means including keys for determining an eye examination mode and for controlling the performance of the eye examination;

on-screen display (OSD) control means for outputting a video signal for an eye examination table corresponding to an eye examination condition determined by the key input means;

switching means for selecting an output signal of the OSD control means and an input video signal to provide the selected signal to a color picture tube (CPT); and control means for controlling the OSD control means and the switching means to display on a screen of the CPT the eye examination table corresponding to a distance for the eye examination and a user's eyesight level when the eye examination distance and the eyesight level are determined by the key input means after the eye examination mode key is entered.

In another aspect of the present invention, there is provided a method for eye examination for a video appliance comprising the steps of:

setting an eye examination mode;

determining a distance for eye examination and a user's eyesight level to be examined;

adjusting the size of each eye examination data constituting an eye examination table corresponding to the determined distance and eyesight; and displaying the adjusted eye examination table on a display screen of the video appliance.

BRIEF EXPLANATION OF THE DRAWINGS

The above object, other features and advantages of the present invention will be more clearly explained by describing the preferred embodiment thereof with reference to the accompanying drawings, in which.

DETAILED DESCRIPTION OF THE PREFERRED EMBODIMENT

Figure 2:
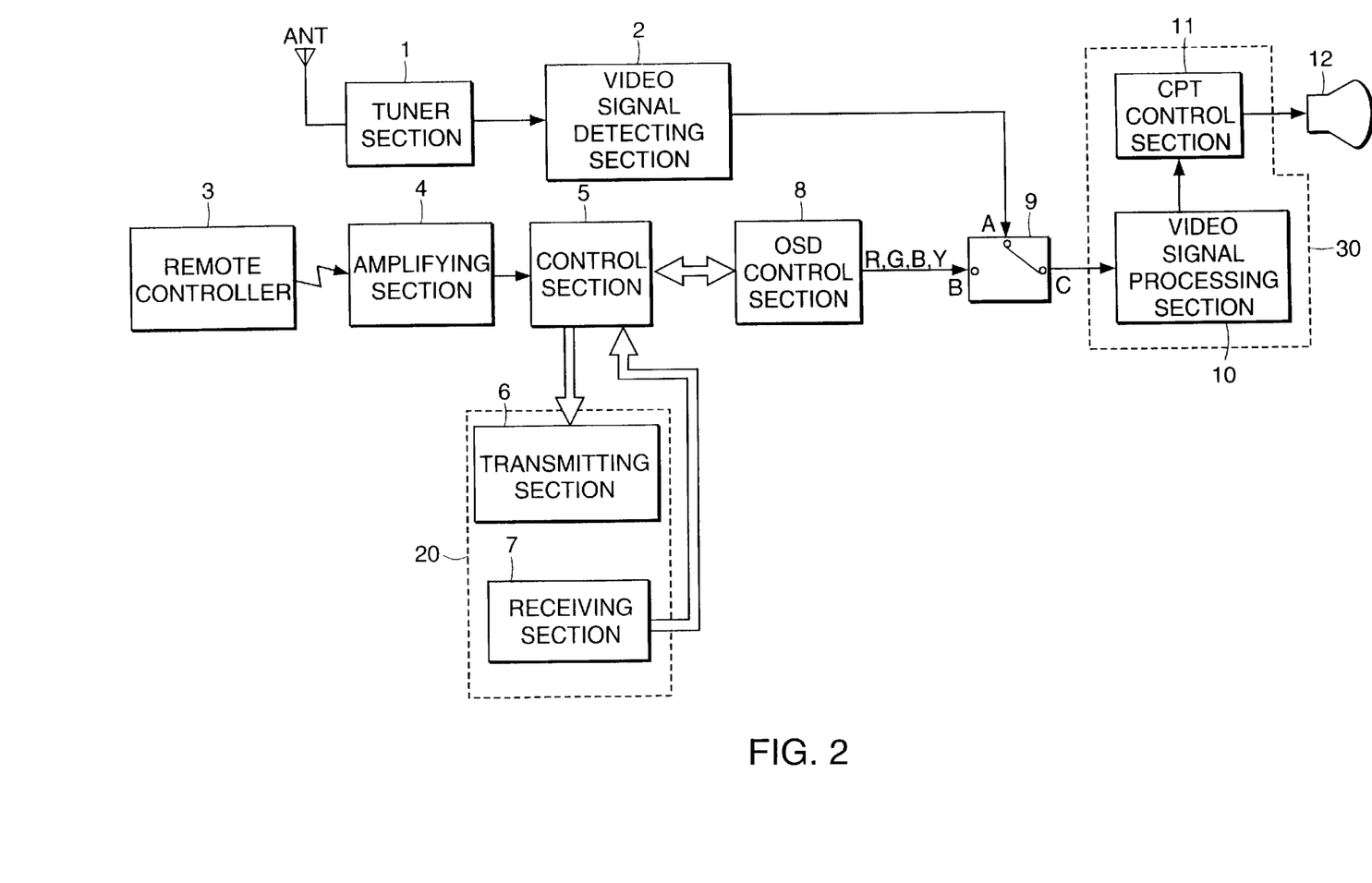
FIG. 2 is a block diagram of an apparatus for eye examination according to the present invention.

Referring to FIG. 2, the eye examination apparatus for a video appliance according to the present invention comprises a tuner section 1 for selecting a desired video signal among composite video signals received by an antenna ANT, a video signal detecting section 2 for detecting the video signal selected by the tuner section 1, a remote controller 3 for controlling the operation of the video appliance as a key input means, an amplifying section 4 for amplifying the output signal of the remote controller 3 with a predetermined amplification factor, a control section 5 for reading the output signal of the amplifying section 4 and providing a corresponding control signal after a distance measuring section 20 for measuring the distance between the video appliance and a user in accordance with the control signal provided from the control section 5, an OSD control section 8 for adjusting and outputting a size of stored eye examination data in accordance with the control signal provided from the control section 5, a switching section 9 for selecting and outputting one of the output signal of the OSC control section 8 and a video signal processed by a video signal detecting section 2 in accordance with the control signal of the control section 5, and a color signal reproducing section 30 for reproducing the output signal of the switching section 9 to provide the reproduced color signal to a CPT 12 of the video appliance.

The distance measuring section 20 comprises an ultrasonic frequency transmitting section 6 for transmitting an ultrasonic frequency according to the control signal of the control section 5, and an ultrasonic frequency receiving section 7 for receiving the ultrasonic frequency, which has been transmitted from the ultrasonic frequency section 6 and reflected by the user, to output the received ultrasonic frequency to the control section 5.

The color signal reproducing section 30 further comprises a video signal processing section 10 for processing the output signal of the switching section 9, and a CPT control section 11 for receiving the output signal of the video signal processing section 10 and adjusting the contrast and color of the video signal to output the adjusted video signal to the CPT 12.

Figure 3:
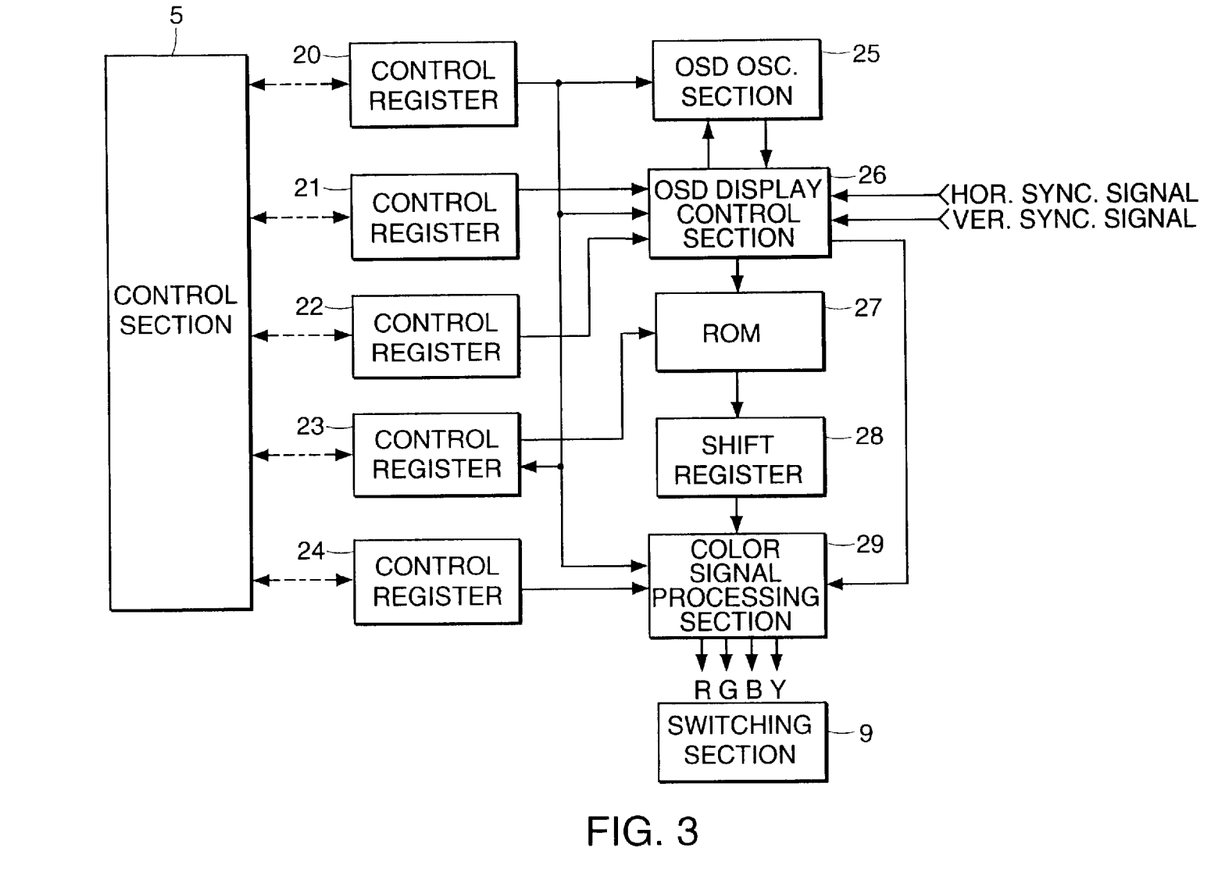
FIG. 3 is a block diagram of the OSD control section in FIG. 2.

As shown in FIG. 3, the OSD control section 8 comprises an OSD control register 20 for storing and outputting data for controlling the OSD according to the control signal of the control section 5, a position control register 21 for storing and outputting data for the position control of the OSD characters displayed on the screen according to the control signal of the control section 5, a character-size control register 22 for storing and outputting data for the size control of the OSD characters displayed on the screen according to the control signal of the control section 5, a color control register 24 for storing and outputting data for the color control of the OSD characters displayed on the screen according to the control signal of the control section 5, an OSD oscillating section 25 for generating pulses for the output of the OSD according to the output signal of the OSD control register 25, a horizontal/vertical OSD display control section 26 for reading the control signals respectively outputted from the OSD control register 20, position control register 21, and the character-size control register 22 in accordance with the horizontal and vertical synchronizing signals, a character read-only memory (ROM) 27 for outputting the eye examination data stored therein according to the signal detected by the OSD display control section 26, a shift register 28 for horizontally shifting the positions of the eye examination data, when required, which have been outputted from the character ROM 27, and a color signal processing section 29 for separating the video data outputted from the shift register 28 into color signals of red (R), green (G), and blue (B) and a luminance signal (Y) according to the output signals from the color control register 24 and the horizontal/vertical OSD display control section 26.

The operation of the apparatus according to the present invention constructed above will be explained with reference to FIGS. 2 to 8.

If a user manipulates the remote controller 3 to operate a TV, the tuner section 1 selects only a desired frequency among the composite video signals received through the antenna. The video signal detection section 2 detects the video signal selected by the tuner section 1 to output the detected video signal to one input terminal A of the switching section 9.

At this time, if the user does not set the eye examination mode, a common contact C of the switching section 9 is connected to the input terminal A of the switching section 9, thereby switching the video signal provided from the video signal detection section 2 to the video signal processing section 10. The video signal processing section 10 processes the video signal to conform to the screen display to provide the processed signal to the CPT control section 11. The CPT control section 11 then outputs the signal to the CPT 12 to display the signal on the screen of the CPT 12.

If the user actuates an eye examination key in the remote controller 3 to select the eye examination mode while viewing the television signal on the screen of the CPT 12, the selected signal is amplified by the amplifying section 4 and then outputted to the control section 5.

Figure 8A:
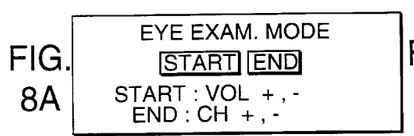
FIGS. 8A to 8H are views explaining the OSD states of the screen according to the present invention.

The control section 5 detects the input eye examination mode, and then controls the OSD control section 8 to notify the user of setting of the eye examination mode by displaying the OSD characters on the screen as shown in FIG. 8A.

The setting process of the eye examination mode will be explained with reference to FIG. 3.

The OSD control register 20 of the OSD control section 8 outputs a control signal for controlling the output of the OSD characters to the OSD oscillating section 25, OSD control section 26, buffer 23 for OSD display, and color signal processing section 29, respectively. The position control register 21 outputs control signals for controlling the position of the OSD image displayed on the screen according to the control signal of the control section 5. The character-size control register 22 outputs control signals for controlling the size of the OSD characters to be displayed to the OSD indicator control section 26.

The OSD oscillating section 25 then provides a predetermined pulse signal for outputting the OSD characters to the OSD control section 26 according to the control signal of the OSD control register 20. The OSD control section 26 detects the control signals provided from the OSD control register 20, position control register 21, and character-size control register 22, respectively, to transmit the corresponding output signals to the color signal processing section 29 through the ROM 27 and shift register 28.

The color control register 24 provides the control signal for controlling the color of the OSD characters to the color signal processing section 29 according to the control signal of the control section 5. The color signal processing section 29 separates the input video signal into the color signals R,G,B and the luminance signal Y according to the color control signal outputted from the color control register 24 to provide the separated signals to an input terminal B of the switching section 9.

The control section 5 controls the switching section 9 so that the contact C of the switching section 9 is connected to the input terminal B thereof, resulting in that the switched color signals R, G, B and the luminance signal Y are provided to the CPT 12 through the video signal processing section 10 and the CPT control section 11 as shown in FIG. 8A.

Figure 8B:
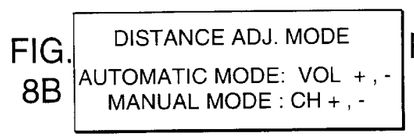

At this time, if the user presses either the (+) or (−) volume key in the remote controller 3, the control section 5 controls the OSD control section 8 to output the OSD characters as shown in FIG. 8B, so that the user can select either an automatic distancing mode or a manual distancing mode. If the user selects the automatic distancing mode and selects either the (+) or (−) volume key for eye examination, the control section 5 perceives the selected automatic distancing mode, and measures the distance between the TV and the user to notify the control section 5 of the measured distance.

The distance measuring between the TV and the user will now be explained.

Figures 7A, 7B:
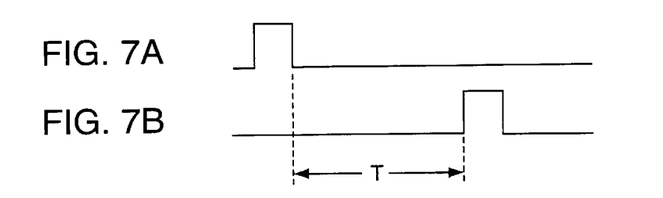
FIGS. 7A and 7B are waveform diagrams illustrating the input/output waveforms of the ultrasonic frequency transmitting and receiving sections when measuring the distance by the distance measuring section in FIG. 2.

The control section 5 outputs a control pulse to the ultrasonic frequency transmitting section 6 for distance measurement as shown in FIG. 7A. Then, the ultrasonic frequency transmitting section 6 transmits an ultrasonic frequency to the ultrasonic receiving section 7. The ultrasonic receiving section 7 receives the ultrasonic frequency which has been outputted from the ultrasonic transmitting section 6 and reflected by the user, and generates a pulse as shown in FIG. 7B to provide the pulse to the control section 5.

If the pulse is inputted to the control section 5 as shown in FIG. 7B, the control section 5 calculates the distance L between the TV and the user based on the time difference T as illustrated in FIGS. 7A and 7B to recognize the calculated data as the distance measurement data given by $$L = Tx \frac{C}{2}$$

where, C equals 340 m/s.

Figure 8C:
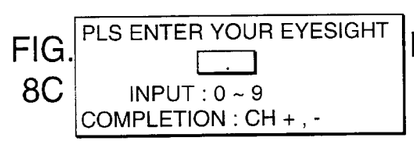

Accordingly, if the user selects an automatic distancing mode, OSD characters are outputted as shown in FIG. 8C. If the user voluntarily selects his/her eyesight to be examined, corresponding OSD characters are outputted as shown in FIG. 8E so that the user can select an examination method.

Figure 4:
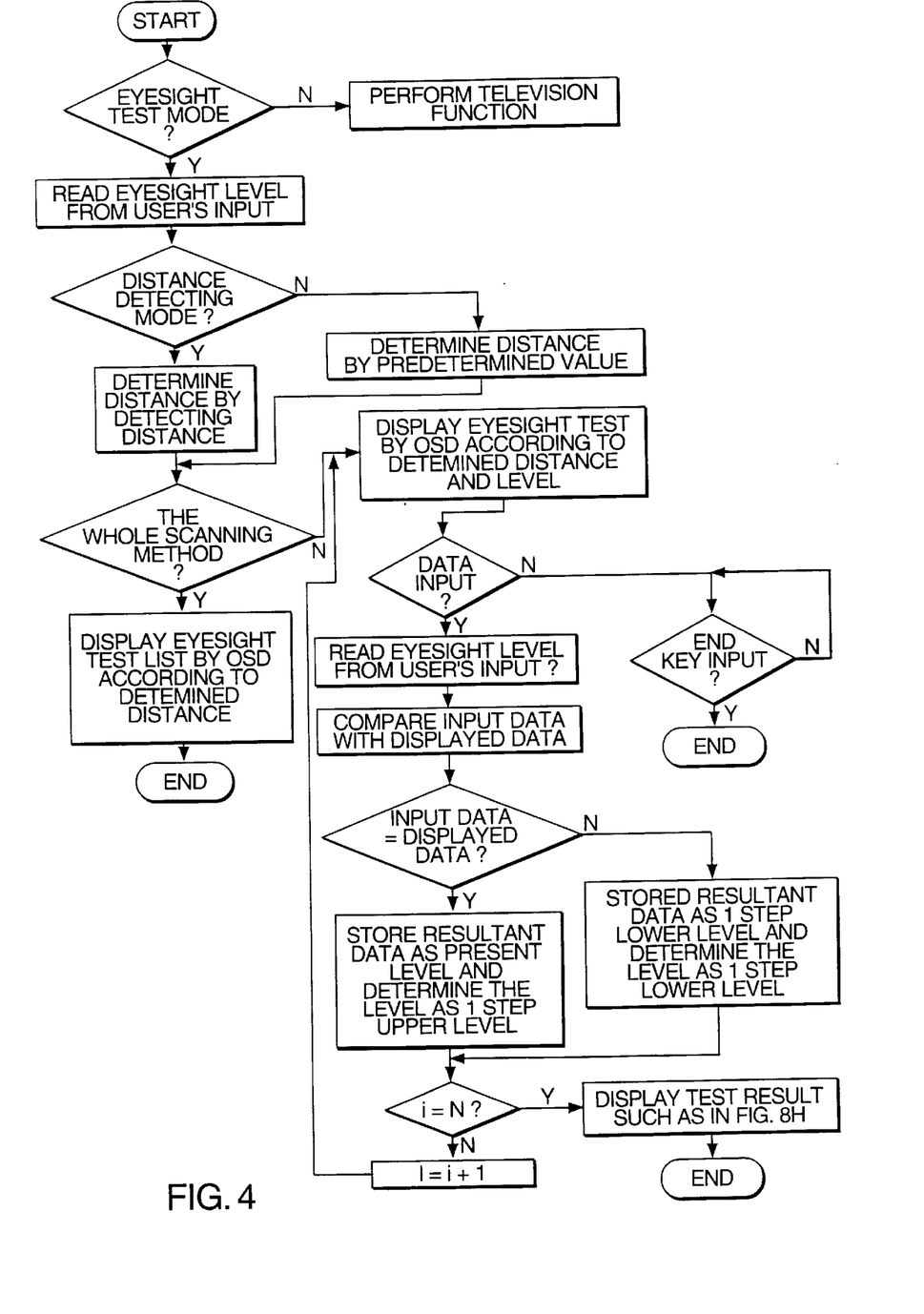
FIG. 4 is a flow diagram explaining the eye examination method according to the present invention.
Figure 8D:
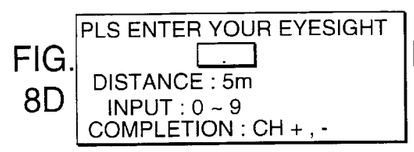
Figure 8E:
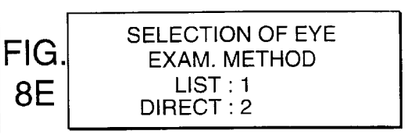
Figure 8F:
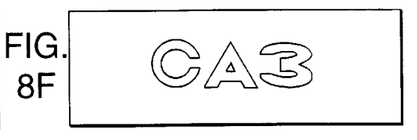

If the user presses either the (+) or (−) channel key to select a manual distancing mode during the output of the OSD characters, the OSD characters are changed to be as shown in FIG. 8D rather than as shown in FIG. 8C. If the user's eyesight is believed to be 1.0, the user should continuously press the keys 1 and 0 of the remote control 3. Then, the eyesight level to be examined will be indicated as 1.0 on the eye examination region of the screen. If the user further presses either the (+) or (−) channel key, the control section 5 recognizes completion of the data input for eye examination, and displays available eye examination methods on the CPT 1 screen. Here, a distance of 5 meters between the TV and the user is a prerequisite for precise eye examination of the user's eyesight in the manual distancing mode. The following description for eye examination method, as illustrated in FIG. 4, is applied both to the automatic distancing mode and manual distancing mode.

If the user selects either a whole scanning or a direct optional examination method appearing on the CPT 12 screen, the control section 5, recognizing the distance between the TV and the user, controls the ROM 27 of the OSD control section 8 to output an eye examination data corresponding to the set distance and the user's eyesight on the CPT 12 screen. In other words, the ROM 27 of the OSD control section 8 storing diverse data of eye examination standards (Landolt Circles, letters and devices) outputs the eye examination data corresponding to the predetermined eyesight to the color signal processing section 29 through the shift register 28 upon receipt of the command for screen display of an eye examination table from the buffer 27 for OSD display which is controlled by the control section 5.

The user can accordingly select a desired eye examination method by pressing a pertinent key of the remote controller, e.g., key "1" for the whole scanning method, or key "2" for the direct optional method.

Figure 5:
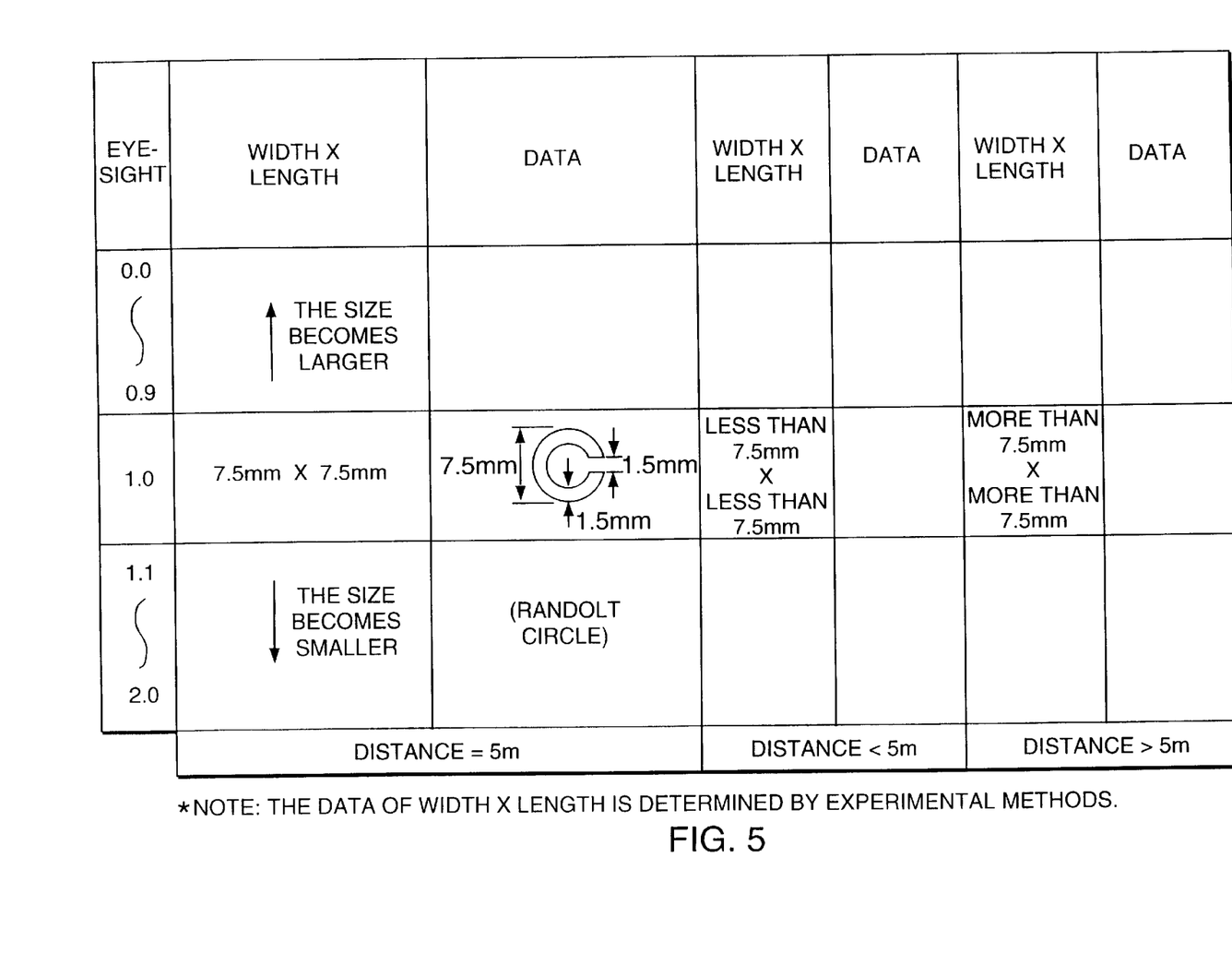
FIG. 5 is a view illustrating an eye examination table explaining the adjustment of the size of the eye examination data according to the eye examination distance.
Figure 6:
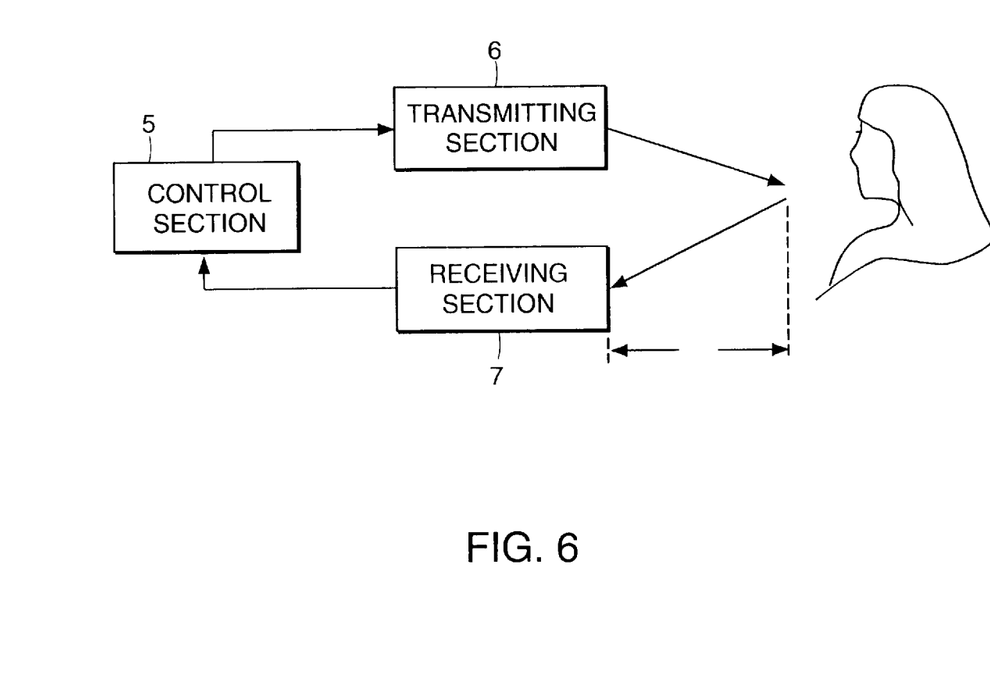
FIG. 6 is a view explaining the measurement of the eye examination distance according to the present invention.

If the user presses the key "1" for the whole scanning method, the control section 5 controls the OSD control section 8 to display on the screen an eye examination table, as illustrated in FIG. 5, comprising Landolt Circles and letters of predetermined size corresponding to the eyesight level of 1.0 inputted by the user. If the user can clearly discern the eye examination datum as shown in FIG. 8, he/she should input an eyesight level higher than 1.0, e.g., 1.2 or 1.5, according to the command as shown in FIG. 8C or 8D for re-examination of his/her own eyesight. If the user cannot clearly discern the eye examination data as shown in FIG. 8, he/she should input any one of the eyesight levels lower than 1.0 among 0.9 through 0.1, according to the command as shown in FIG. 8C or 8D for re-examination of his/her own eyesight.

Figure 8G:
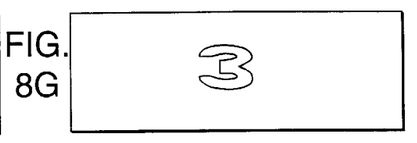

If the user presses the key 2 to select a direct optional method under the display of the OSD characters as shown in FIG. 8E, a numeral (any one of 0 to 9) or a letter of predetermined size corresponding to the eyesight level of 1.0 is displayed on the screen as shown in FIG. 8G. If the user inputs the same numeral or letter as displayed on the screen by pressing the keys on the remote controller 3, the control section 5 detects the data inputted by the user. If the input data differs from the numeral or letter displayed on the screen, the control section 5 displays a numeral or letter corresponding to the one-level lower eyesight. If the input data is identical to the numeral or letter displayed on the screen, the control section 5 displays a numeral or letter corresponding to the one-level higher eyesight.

The user can confirm his/her own eyesight by repeating the above eye examination procedures as many times as required.

Figure 8H:
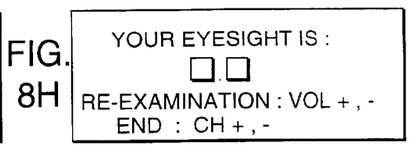

If the user presses a channel key to return to the original TV function, his/her eyesight is notified on the screen as shown in FIG. 8H. Pressing the channel key again restores the original TV function out of the eye examination mode.

As described above, the present invention provides an apparatus and method for eye examination, whereby a program required for eye examination is preset in the control section 5, and eye examination data including the Landolt Circles are preset in the OSD control section 8, and the user voluntarily selects an ideal distance for eye examination and an eyesight with the eye examination keys, thereby an eye examination table corresponding to the selected distance and eyesight appears on the CPT screen. This method enables the user to conduct an eye examination by means of a video appliance whenever required.

While the present invention has been described and illustrated herein with reference to the preferred embodiment thereof, it will be understood by those skilled in the art that various changes in form and details may be made therein without departing from the spirit and scope of the invention.

What is claimed is:

1. An apparatus for eye examination by a video appliance, comprising:

an input device for selecting an eye examination mode by a user;

a video display for viewing images;

an on-screen display (OSD) source for outputting symbols to be displayed on said display means; and a controller for controlling the OSD source, said controller being responsive to selection of the eye examination mode to determine the characteristics of an eye examination symbol to be displayed on the video display through the OSD source.

2. The apparatus as claimed in claim 1 further comprising a distance measurement system for measuring a distance between the video display and the user, wherein the controller varies the characteristics of the symbols as a function of the distance between the user and the video display.

3. The apparatus for eye examination as claimed in claim 1, wherein the input device is a remote controller.

4. The apparatus for eye examination as claimed in claim 1, further comprising a distance measuring system for automatically measuring distance between the user and the video display.

5. The apparatus for eye examination as claimed in claim 4, wherein the distance measuring system comprises:

an ultrasonic frequency transmitter for transmitting an ultrasonic frequency according to the control signal of the controller; and an ultrasonic frequency receiver for receiving the ultrasonic frequency, which has been transmitted by the ultrasonic frequency transmitter and then reflected by an object, to provide the received ultrasonic frequency to the controller.

6. The apparatus for eye examination as claimed in claim 1, wherein the eye examination symbol is one or more of the Landolt Circles, devices, and numerals.

7. The apparatus for eye examination as claimed in claim 1, wherein the eye examination symbol comprises one or more of the numerals or letters included in the input device, and is displayed at predetermined intervals under the control of the controller.

8. The apparatus for eye examination as claimed in claim 7, wherein the controller compares an eye examination symbol voluntarily selected by the user through the input device with the displayed eye examination symbol to notify the user of the compared value and display another eye examination symbol.

9. A method for eye examination by a video appliance, comprising the steps of:

receiving selection of an eye examination mode by a user;

determining a distance between a display screen of the video appliance and the user in response to the user's selection;

determining the characteristics of an eye examination symbol to be displayed, the characteristics varying as a function of the determined distance; and displaying the eye examination symbol on the display screen of the video appliance according to the determined characteristics.

10. The method for eye examination as claimed in claim 9, further comprising the step of repeatedly changing the characteristics of the eye examination symbols to obtain an accurate eye examination of the user.

11. The method for eye examination as claimed in claim 9, wherein an ideal distance for examination is set by selecting, by the user, either an automatic distancing mode or a manual distancing mode.

12. The method for eye examination as claimed in claim 11, wherein the distance determining step includes automatically measuring the distance between the display screen and the user when the automatic distancing mode is selected.

13. The method for eye examination as claimed in claim 9, wherein the eye examination symbol is one or more of the Landolt Circles, letters, and devices.

14. The method for eye examination as claimed in claim 9, wherein the eye examination symbol is a table and the step of displaying the eye examination symbol comprises the steps of:

displaying one eye examination table among a plurality of tables in turn at predetermined intervals;

receiving data related to the displayed eye examination table from the user;

comparing the displayed eye examination table with the received data; and notifying the user of an eyesight corresponding to the comparison.

15. The method for eye examination as claimed in claim 14, wherein the step of displaying the eye examination table further comprises the substeps of:

displaying an eye examination table one-level lower than the previously displayed eye examination table when a compared value is higher than the set value; and displaying an eye examination table one-level higher than the previously displayed eye examination table when the compared value is lower than the set value.

16. The method for eye examination as claimed in claim 14, wherein the eye examination data comprises either letters or numerals included in a remote controller of the video appliance.

17. The method for eye examination as claimed in claim 14, wherein the received data is inputted by means of a remote controller of the video appliance.

* * * * *